US010852292B2

(12) United States Patent
Sato et al.

(10) Patent No.: US 10,852,292 B2
(45) Date of Patent: Dec. 1, 2020

(54) SEMICONDUCTOR APPARATUS AND POTENTIAL MEASURING APPARATUS

(71) Applicant: SONY SEMICONDUCTOR SOLUTIONS CORPORATION, Kanagawa (JP)

(72) Inventors: Masahiro Sato, Tokyo (JP); Machiko Kametani, Tokyo (JP); Jun Ogi, Kanagawa (JP); Yuri Kato, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 0 days.

(21) Appl. No.: 16/343,598

(22) PCT Filed: Nov. 17, 2017

(86) PCT No.: PCT/JP2017/041416
§ 371 (c)(1),
(2) Date: Apr. 19, 2019

(87) PCT Pub. No.: WO2018/101075
PCT Pub. Date: Jun. 7, 2018

(65) Prior Publication Data
US 2020/0049688 A1    Feb. 13, 2020

(30) Foreign Application Priority Data

Dec. 2, 2016   (JP) .................................. 2016-235130

(51) Int. Cl.
*G01N 33/483*    (2006.01)
*G01N 27/27*    (2006.01)
(Continued)

(52) U.S. Cl.
CPC ......... *G01N 33/4836* (2013.01); *G01N 27/27* (2013.01); *G01N 27/30* (2013.01);
(Continued)

(58) Field of Classification Search
CPC .... G01N 33/4836; G01N 27/27; G01N 27/30; G01N 33/48728; H01L 27/0255; H03F 1/52
(Continued)

(56) References Cited

U.S. PATENT DOCUMENTS 6,476,751 B1 * 11/2002 Krymski ............. H03M 1/1014
341/120
7,030,801 B2 * 4/2006 Luo ........................ H03M 1/682
341/155
(Continued)

FOREIGN PATENT DOCUMENTS

| CA | 2743258 A1 | 5/2010 |
| CN | 102272593 A | 12/2011 |

(Continued)

OTHER PUBLICATIONS

International Search Report and Written Opinion of PCT Application No. PCT/JP2017/041416, dated Jan. 30, 2018, 09 pages of ISRWO.
(Continued)

*Primary Examiner* — Giovanni Astacio-Oquendo
(74) *Attorney, Agent, or Firm* — Chip Law Group

(57) ABSTRACT

The present disclosure relates to a semiconductor apparatus and a potential measuring apparatus capable of preventing electrostatic breakdown in an electrode formation process when an electrode and an amplifier are provided on a same substrate. A diode is provided of which a cathode is connected to a previous stage of an amplifying transistor for amplifying a signal read by a read electrode for reading a (Continued)

potential having contact with liquid in which a specimen is input and an anode is grounded. With such a configuration, by bypassing a negative charge generated between the electrode and the amplifying transistor in the electrode formation process from the diode and discharging the negative charge toward ground so as to prevent electrostatic breakdown. This is applicable to a bioelectric potential measuring apparatus.

13 Claims, 9 Drawing Sheets

(51) Int. Cl.
    *G01N 27/30*     (2006.01)
    *G01N 33/487*     (2006.01)
    *H01L 27/02*     (2006.01)
    *H03F 1/52*     (2006.01)

(52) U.S. Cl.
    CPC ... *G01N 33/48728* (2013.01); *H01L 27/0255* (2013.01); *H03F 1/52* (2013.01)

(58) Field of Classification Search
    USPC .......................... 324/713, 111, 76, 112, 120
    See application file for complete search history.

(56) References Cited

U.S. PATENT DOCUMENTS

| | | | |
|---|---|---|---|
| 7,786,908 B2 * | 8/2010 | Yoshinaga | H03M 1/1023 341/118 |
| 2012/0091011 A1 | 4/2012 | Graham et al. | |
| 2013/0300435 A1 | 11/2013 | Chi et al. | |
| 2014/0142458 A1 | 5/2014 | Leyde et al. | |
| 2014/0375338 A2 | 12/2014 | Chi et al. | |

FOREIGN PATENT DOCUMENTS

| | | |
|---|---|---|
| EP | 2356448 A1 | 8/2011 |
| JP | 06-078889 A | 3/1994 |
| JP | 2002-031617 A | 1/2002 |
| JP | 2012-508051 A | 4/2012 |
| JP | 2013-011482 A | 1/2013 |
| JP | 2013-092437 A | 5/2013 |
| JP | 5769020 B2 | 8/2015 |
| JP | 5796373 B2 | 10/2015 |
| WO | 2010/055287 A1 | 5/2010 |
| WO | 2011/153216 A2 | 12/2011 |

OTHER PUBLICATIONS

Mestais, et al., "WIMAGINE: Wireless 64-Channel ECOG Recording Implant for Long Term Clinical Applications", Transactions on Neural Systems and Rehabilitation Engineering, IEEE, vol. 23, No. 1, Jan. 2015, pp. 10-21.

Extended European Search Report of EP Application No. 17875539.3, dated Nov. 14, 2019, 11 pages.

* cited by examiner

SEMICONDUCTOR APPARATUS AND POTENTIAL MEASURING APPARATUS

CROSS REFERENCE TO RELATED APPLICATIONS

This application is a U.S. National Phase of International Patent Application No. PCT/JP2017/041416 filed on Nov. 17, 2017, which claims priority benefit of Japanese Patent Application No. JP 2016-235130 filed in the Japan Patent Office on Dec. 2, 2016. Each of the above-referenced applications is hereby incorporated herein by reference in its entirety.

TECHNICAL FIELD

The present disclosure relates to a semiconductor apparatus and a potential measuring apparatus, and more particularly, to a semiconductor apparatus and a potential measuring apparatus capable of preventing electrostatic breakdown during manufacturing.

BACKGROUND ART

In recent years, a technology for measuring an action potential of nerve cells and contributing to medical research regarding the nerve action has been required. For example, an electrode apparatus for measuring and recording the action potential of the nerve cells has been proposed (refer to Patent Documents 1 and 2).

CITATION LIST

Patent Document

Patent Document 1: Japanese Patent Application Laid-Open No. 06-078889
Patent Document 2: Japanese Patent Application Laid-Open No. 2002-031617

SUMMARY OF THE INVENTION

Problems to be Solved by the Invention

In the technologies described in Patent Documents 1 and 2, the measured potential measured by the electrode is output to an amplifier provided outside the apparatus and amplified to be output.

Whereas, in response to a request for miniaturizing the apparatus in recent years, it has been considered to miniaturize the amplifier (amplifying transistor) and provide the amplifier on the same substrate as the electrode to miniaturize the apparatus.

However, if the amplifier is miniaturized, an input capacitance is reduced. Therefore, there is a concern about electrostatic breakdown during manufacturing.

The present disclosure has been made in consideration of such circumstances, and in particular, prevents the electrostatic breakdown during manufacturing caused by miniaturization of the amplifier regarding the measured potential in the potential measuring apparatus.

Solutions to Problems

A semiconductor apparatus according to one aspect of the present disclosure includes a reference potential generating unit and a reference potential electrode that supply a reference potential to liquid, a read electrode and an amplifier that read a signal from the liquid, and a protection portion that protects the amplifier from a negative charge at a previous stage of the amplifier, in which the reference potential generating unit, the reference potential electrode, the read electrode, the amplifier, and the protection portion are installed on a same substrate.

It is possible that the protection portion bypasses generated negative charges to the amplifier via a wiring connected to the read electrode and the reference potential electrode at a time of an electrode formation process for forming the read electrode and the reference potential electrode to protect the amplifier.

The amplifier can be an amplifying transistor, the read electrode can be connected to a gate of the amplifying transistor, and the protection portion can be a protection diode of which a cathode is connected to a previous stage of the gate on the wiring for connecting the read electrode and the amplifying transistor, and an anode is grounded.

It is possible that an additional protection portion can be included, of which an anode is connected to the cathode of the protection diode, a cathode is connected to a predetermined power source, having IV (current voltage) characteristics same as the protection diode.

A voltage of the predetermined power source can be higher than the reference potential.

The predetermined power source can be a power source of the amplifying transistor.

Another protection portion can be included that protects the amplifier from a negative charge at a previous stage of the reference potential generating unit.

It is possible that the another protection portion bypasses the generated negative charge to the reference potential generating unit via wiring connected to the reference potential electrode and the reference potential generating unit at a time of an electrode formation process for forming the read electrode and the reference potential electrode to protect the reference potential generating unit.

The another protection portion can be another protection diode of which a cathode is connected to a previous stage of the reference potential generating unit on the wiring for connecting the reference potential electrode and the reference potential generating unit and an anode is grounded.

Another additional protection portion including another additional diode can be included, of which an anode is connected to the cathode of the diode, a cathode is connected to a predetermined power source, having IV (current voltage) characteristics same as the another protection diode.

A voltage of the predetermined power source can be higher than the reference potential.

The predetermined power source can be a power source of the amplifying transistor.

A potential measuring apparatus according to one aspect of the present disclosure includes a reference potential generating unit and a reference potential electrode that supply a reference potential to liquid, a read electrode and an amplifier that read a signal from the liquid, and a protection portion that protects the amplifier from a negative charge at a previous stage of the amplifier, in which the reference potential generating unit, the reference potential electrode, the read electrode, the amplifier, and the protection portion are installed on a same substrate.

According to one aspect of the present disclosure, a reference potential generating unit and a reference potential electrode supply a reference potential to liquid, a read electrode and an amplifier read a signal from the liquid, a protection portion protects the amplifier from a negative charge at a previous stage of the amplifier, and the reference potential generating unit, the reference potential electrode, the read electrode, the amplifier, and the protection portion are installed on a same substrate.

Effects of the Invention

According to one aspect of the present disclosure, it is possible to prevent electrostatic breakdown during manufacturing due to miniaturization of an amplifier of a measured potential in a potential measuring apparatus.

MODE FOR CARRYING OUT THE INVENTION

Figure 1:
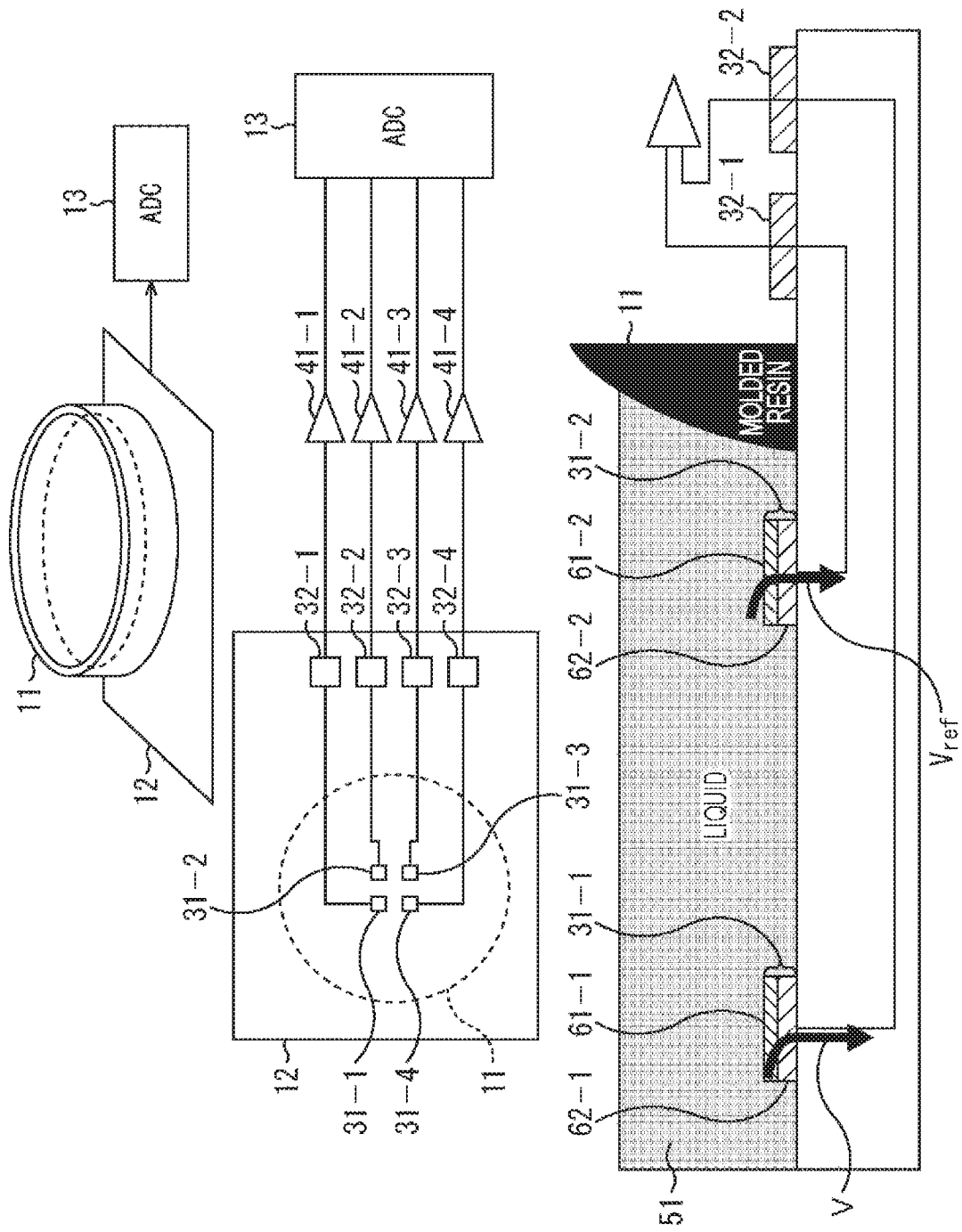
FIG. 1 is a diagram for explaining an exemplary configuration of a general potential measuring apparatus.

Hereinafter, preferred embodiments of the present disclosure will be described in detail with reference to the accompanying drawings. Note that, in the present specification and the drawings, components having substantially the same functional configuration are denoted with the same reference numeral so as to omit redundant description.

<Exemplary Configuration of General Potential Measuring Apparatus>

In description of a potential measuring apparatus according to the present disclosure, first, an exemplary configuration of a general potential measuring apparatus will be described with reference to FIG. 1. An upper part of FIG. 1 is a schematic perspective diagram of a potential measuring apparatus 1, a middle part of FIG. 1 is a wiring diagram corresponding to a top view of a petri dish 11 and an electrode substrate 12, and a lower part of FIG. 1 is a wiring diagram of a side cross section of the potential measuring unit 1.

As illustrated in the upper part of FIG. 1, the potential measuring apparatus 1 includes the petri dish 11, the electrode substrate 12, and an Analog Digital Converter (ADC) 13. The petri dish 11 includes molded resin and is filled with liquid 51 such as normal saline, and cells to be specimens are input to the petri dish 11. As illustrated in the middle part of FIG. 1, electrodes 31-1 to 31-4 are provided on a bottom surface of the petri dish 11 and respectively output measured potentials to amplifiers 41-1 to 41-4 via terminals 32-1 to 32-4. The amplifiers 42-1 to 42-4 amplify the measured potentials supplied from the electrodes 31-1 to 31-4 and output the measured potentials to the ADC 13. The ADC 13 converts the measured potentials which are amplified analog signals supplied from the amplifiers 42-1 to 42-4 into digital signals and output the digital signals to a subsequent apparatus.

In other words, a change in an action potential of a cell as a specimen in the liquid 51 is detected by the electrodes 31-1 to 31-4 and output to the ADC 13 via the terminals 32-1 to 32-4 and the amplifiers 41-1 to 41-4 as the digital signals.

Note that, in a case where it is not necessary for the electrodes 31-1 to 31-4, the terminals 32-1 to 32-4, and the amplifiers 41-1 to 41-4 to be particularly distinguished from each other, the electrodes 31-1 to 31-4, the terminals 32-1 to 32-4, and the amplifiers 41-1 to 41-4 are respectively and simply referred to as an electrode 31, a terminal 32, and an amplifier 41, and other components are similarly referred.

Furthermore, as illustrated in the lower part of FIG. 1, the electrodes 31-1 and 31-2 respectively include, for example, plating portions 61-1 and 61-2 and terminals 62-1 and 62-2, and plating processing is performed on the terminals 62-1 and 62-2 to add the plating portions 61-1 and 61-2, and the plating portions 61-1 and 61-2 have contact with the liquid 51. Note that, although not illustrated, the same applies to the electrodes 31-3 and 31-4.

In other words, in a case where a local potential change around the electrode 31-1 is measured, the measured potential of the electrode 31-2 is read from the terminal 32-2, and an average potential is compared with the measured potential supplied from the electrode 32-1 via the terminal 32-1 as a reference potential Vref so as to measure a local potential change in the vicinity of the electrode 31-1.

However, in a case where the apparatus configuration is miniaturized by providing the amplifier directly below the electrode 31, that is, in the same substrate as the electrode 31 in response to a request for miniaturizing the apparatus, for example, if the amplifier is an amplifying transistor, it is necessary to reduce the capacity of the amplifying transistor. Therefore, the electrostatic breakdown easily occurs during manufacturing.

Therefore, the potential measuring apparatus according to the present disclosure prevents the electrostatic breakdown of the amplifier during manufacturing.

<Exemplary Configuration of Top surface of Potential Measuring Apparatus of Present Disclosure>

An exemplary configuration of the potential measuring apparatus which is a semiconductor apparatus according to the present disclosure will be described with reference to FIG. 2. Note that, in FIG. 2, a configuration of a substrate 110 of a potential measuring apparatus 101 is illustrated, and a configuration corresponding to the top view of the electrode substrate 12 in the middle part of FIG. 1 is illustrated.

Figure 2:
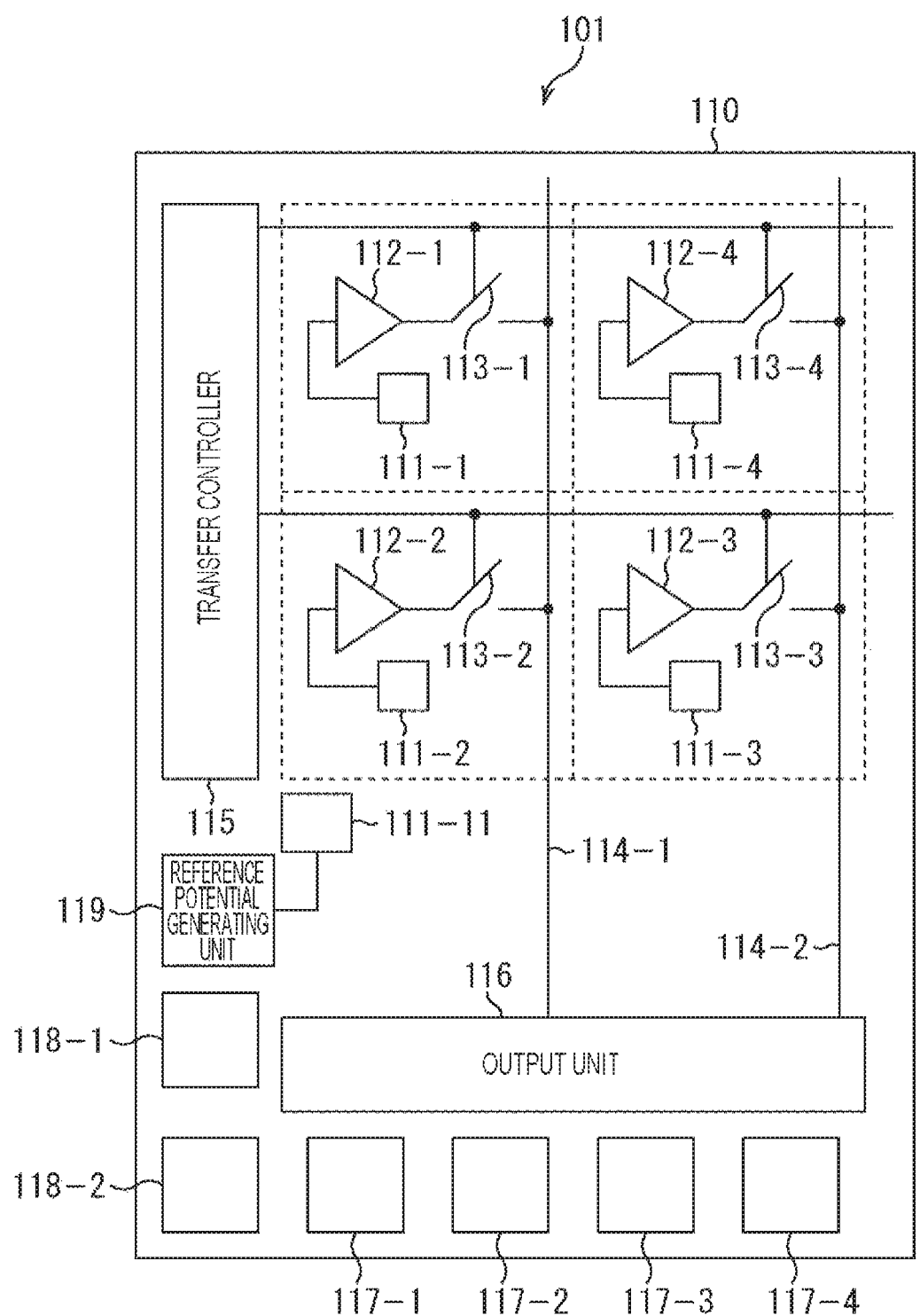
FIG. 2 is a diagram for explaining an exemplary configuration of a potential measuring apparatus according to the present disclosure.

The potential measuring apparatus 101 in FIG. 2 includes electrodes 111-1 to 111-4 and 111-11, amplifiers 112-1 to 112-4, switches 113-1 to 113-4, vertical transfer lines 114-1 and 114-2, a transfer controller 115, an output unit 116, terminals 117-1 to 117-4, terminals 118-1 and 118-2, and a reference potential generating unit 119.

The electrodes 111-1 to 111-4 and 111-11 are provided in the petri dish 11 including molded resin, and the electrodes 111-1 to 111-4 respectively correspond to the electrodes 31-1 to 31-4. The electrodes 111-1 to 111-4 have contact with liquid 131 (FIG. 3) in the petri dish 11 including molded resin, measure an action potential of a specimen in the liquid 131, and respectively transmits the action potential to the amplifiers 112-1 to 112-4. Furthermore, the electrode 111-11 supplies a reference potential generated by the reference potential generating unit 119 to the liquid 131.

The amplifiers 112-1 to 112-4 are respectively provided directly below the electrodes 111-1 to 111-4 in the single substrate and respectively amplify voltages detected by the electrodes 111-1 to 111-4 and output the detected voltages to the switches 113-1 to 113-4.

The switches 113-1 and 113-2 are controlled to be turned on or off by the transfer controller 115. When being turned on, the switches 113-1 and 113-2 output outputs from the amplifiers 112-1 and 112-2 to the output unit 116 via the vertical transfer line 114-1. The switches 113-3 and 113-4 are controlled to be turned on or off by the transfer controller 115. When being turned on, the switches 113-3 and 113-4 output outputs from the amplifiers 112-3 and 112-4 to the output unit 116 via the vertical transfer line 114-2.

The output unit 116 converts amplified signals supplied from the amplifiers 112-1 to 112-4 via the vertical transfer lines 114-1 and 114-2 into digital signals and outputs the digital signals from the terminals 117-1 to 117-4.

The terminals 118-1 and 118-2 receive power and the like supplied from outside.

The reference potential generating unit 119 generates the reference potential and supplies the reference potential to the liquid 131 by the electrode 111-11. The electrode 111-11 has contact with the liquid 131 (FIG. 3) in the petri dish 11 including molded resin and supplies the reference potential to the liquid 131.

<First Protection Circuit in Potential Measuring Apparatus>

Figure 3:
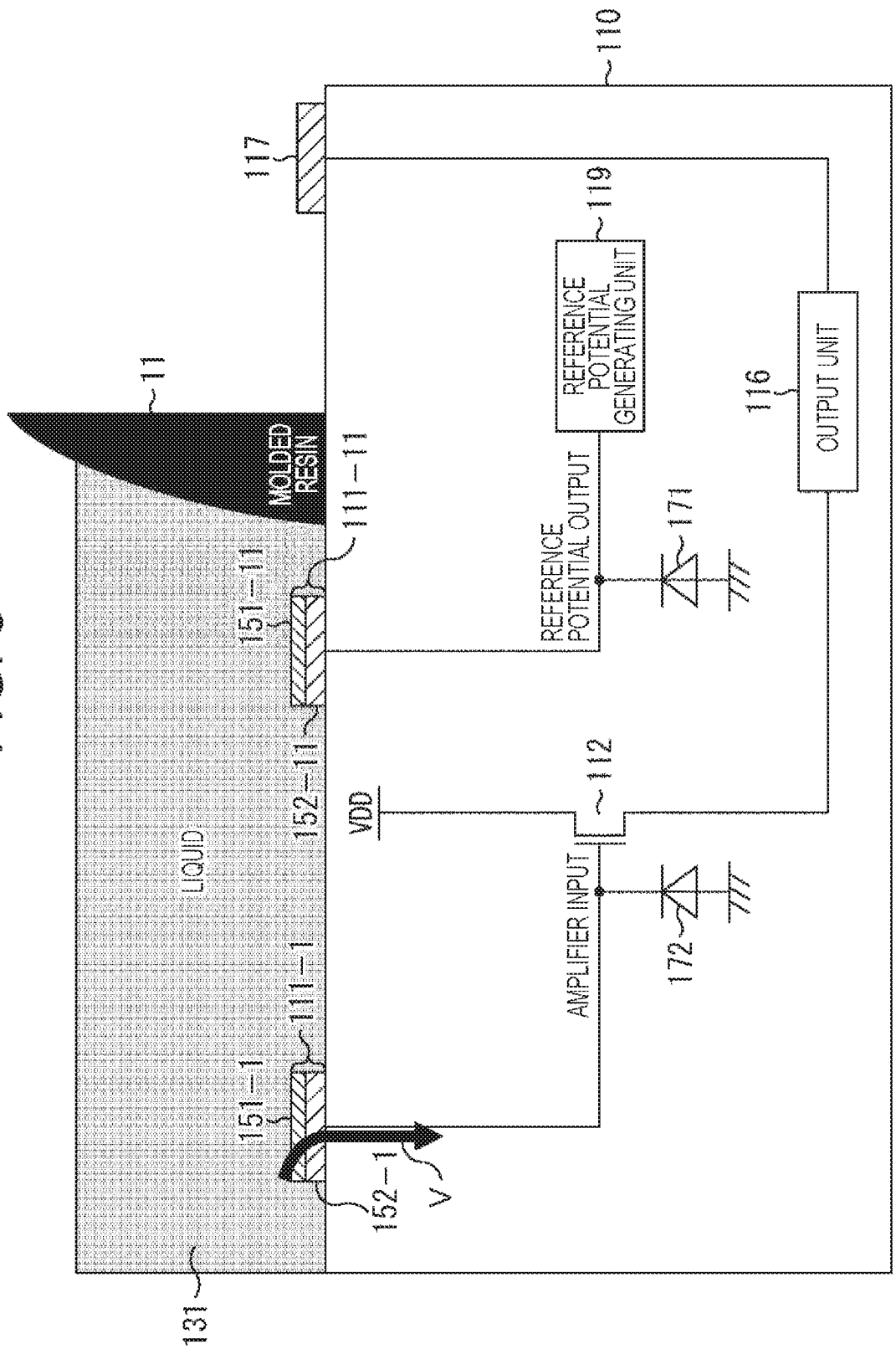
FIG. 3 is a diagram for explaining an exemplary configuration of a first protection circuit of the potential measuring apparatus in FIG. 2.

Next, an exemplary configuration of a protection circuit of the amplifier 112 in the potential measuring apparatus 101 will be described with reference to FIG. 3. FIG. 3 illustrates a side cross section of the potential measuring apparatus 101.

The electrodes 111-1 and 111-11 respectively include plating portions 151-1 and 151-11 including platinum and the like and metal portions 152-1 and 152-11. The electrode 111 includes only the metal portion 152 in general. However, since the metal portion 152 is a portion having contact with the liquid 131, the plating portion 151 is provided to prevent corrosion and the like.

The electrode 111-1 is an electrode which reads a signal, is connected to a gate of the amplifier 112 including an amplifying transistor, and transmits a potential of the liquid 131. The amplifier 112 includes an amplifying transistor, and a source and a drain of the amplifying transistor are connected to a power source VDD. The amplifier 112 outputs a voltage according to a potential V supplied from the electrode 111-1 to the gate to the output unit 116.

The output unit 116 analog-digital converts the output voltage which is the analog signal from the amplifier 112 and outputs the digital signal from the terminal 117.

Furthermore, the electrode 111-11 is an electrode which applies the reference potential output from the reference potential generating unit 119 to the liquid 131.

A diode 171 is provided near the reference potential generating unit 119 and is connected in a state where a cathode is connected to the electrode 111-11 and the reference potential generating unit 119 and an anode is grounded.

The diode 171 prevents negative charges generated at the time of an electrode formation process for forming the electrodes 111-1 and 111-11 from flowing into the reference potential generating unit 119 so as to prevent the electrostatic breakdown of the reference potential generating unit 119 at the time of manufacturing.

A diode 172 is provided near the amplifier 112 and is connected in a state where a cathode is connected to the electrode 111-1 and the gate of the amplifying transistor and an anode is grounded.

The diode 172 bypasses the negative charges generated at the time of the electrode formation process of the electrodes 111-1 and 111-11 to the ground and discharges the negative charges to prevent the negative charges from flowing into the gate of the amplifying transistor configuring the amplifier 112 so as to prevent the electrostatic breakdown of the amplifying transistor configuring the amplifier 112 at the time of manufacturing.

As a result, by bypassing the negative charges at the time of the electrode formation process to the ground by the diodes 171 and 172, it is possible to prevent the electrostatic breakdown of the amplifying transistor configuring the amplifier 112 and the reference potential generating unit 119.

<Second Protection Circuit in Potential Measuring Apparatus>

In the above, an example has been described in which, by providing the diodes 171 and 172 at the previous stage of the reference potential generating unit 119 and the gate of the amplifying transistor configuring the amplifier 112, the negative charges generated at the time of the electrode formation process are prevented from flowing from the electrodes 111-1 and 111-11 into the reference potential generating unit 119 and the gate of the amplifying transistor configuring the amplifier 112 so as to prevent the electrostatic breakdown of the reference potential generating unit 119 and the amplifying transistor configuring the amplifier 112.

Figure 4:
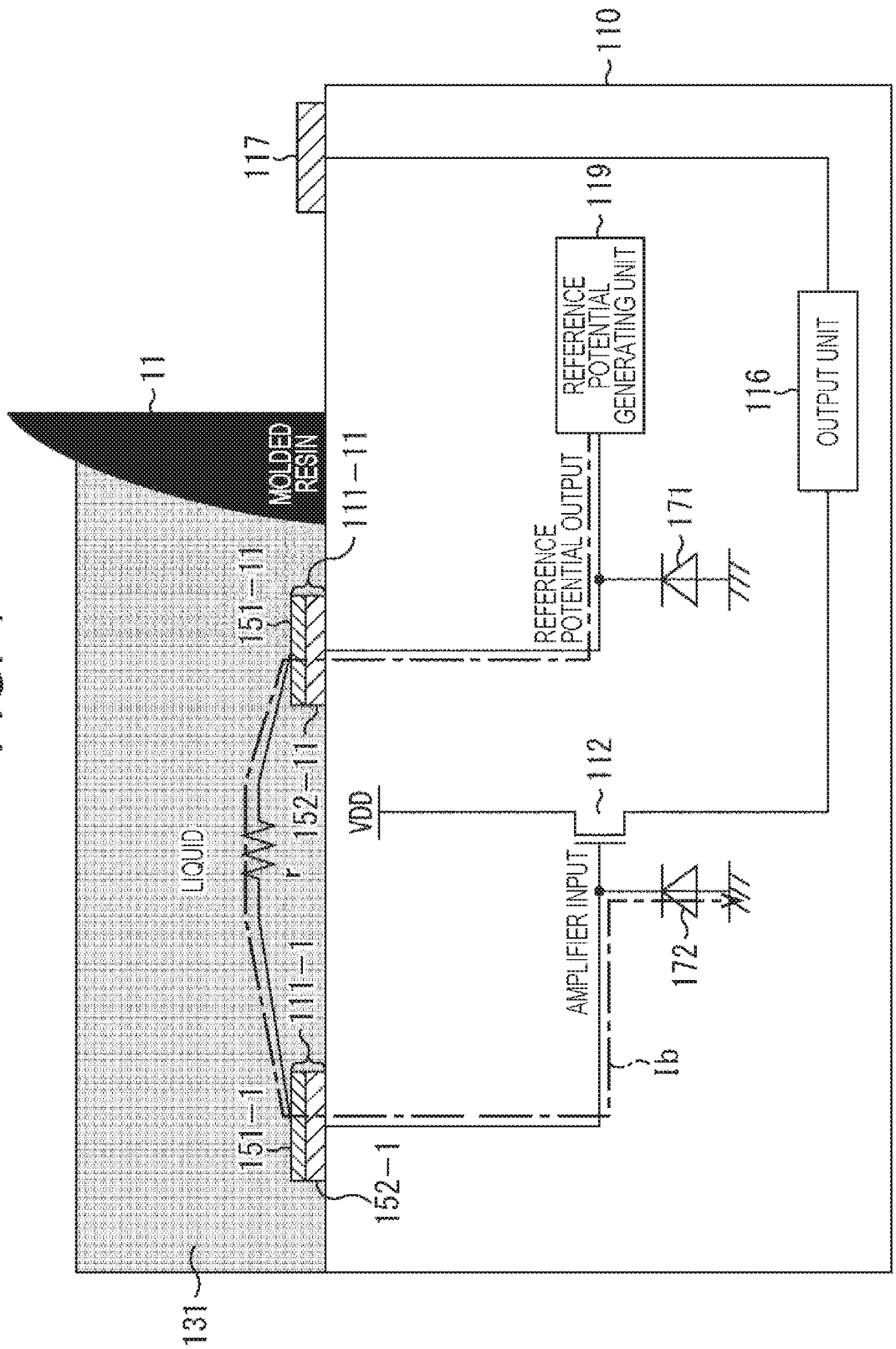
FIG. 4 is a diagram for explaining an operation of the first protection circuit of the potential measuring apparatus in FIG. 2.

However, in a case of the configuration in FIG. 3, as illustrated in FIG. 4, since an impedance of the reference potential generating unit 119 is small, when the reference potential generating unit 119 generates a reference potential to read a signal, there is a possibility that a leakage current Ib indicated by an alternate long and short dash line is generated by the diode 171 which is a negative charge protection circuit and is flowed into the reference potential generating unit 119, a potential difference from the reference potential is generated by the external resistance r by the liquid 131, and the input potential to the gate of the amplifying transistor configuring the amplifier 112 differs from the reference potential. With this operation, when the leakage current Ib and the external resistance r vary, the input potential to the gate of the amplifier 112 varies.

Figure 5:
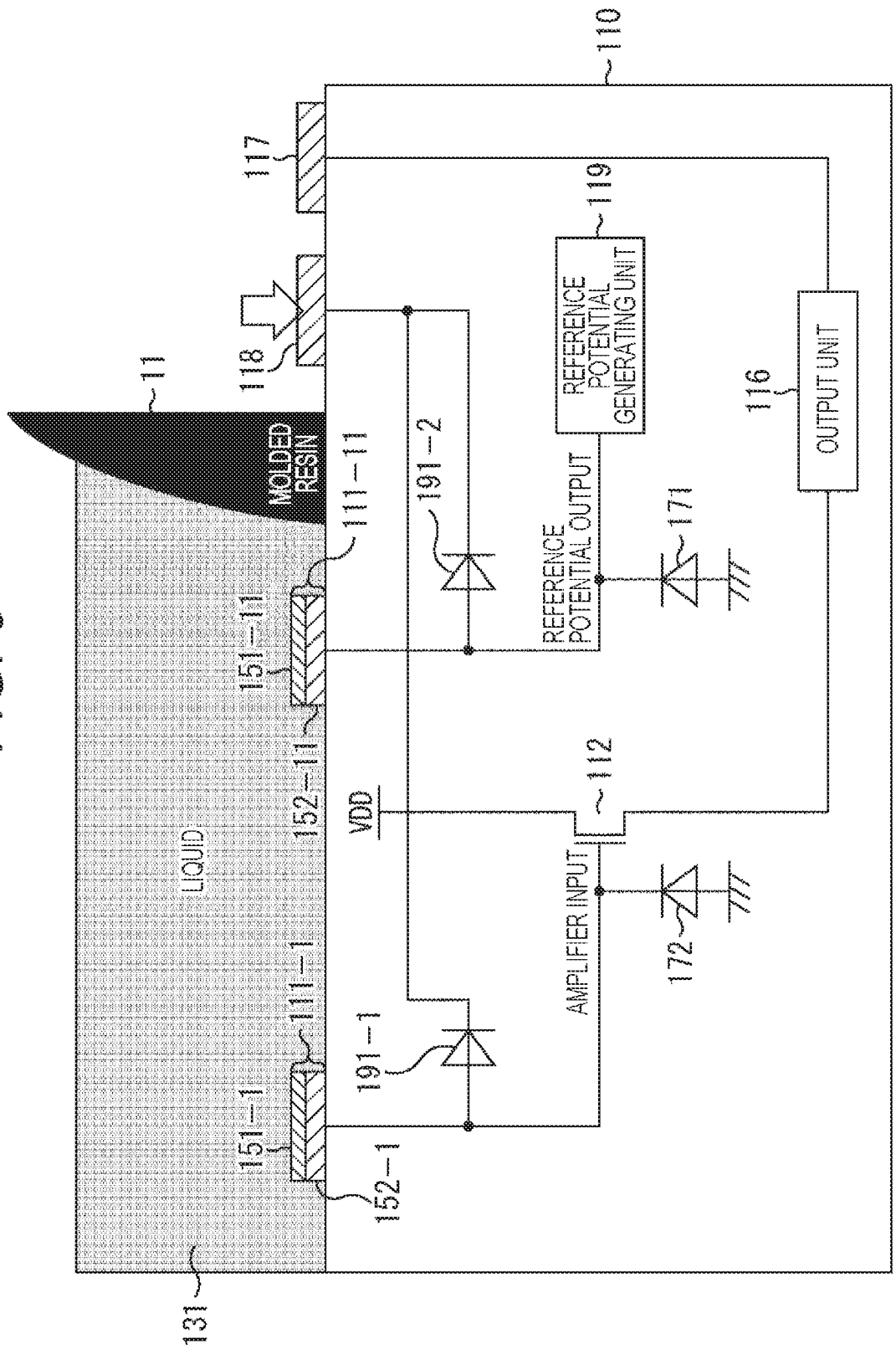
FIG. 5 is a diagram for explaining an exemplary configuration of a second protection circuit of the potential measuring apparatus in FIG. 2.

Therefore, as illustrated in FIG. 5, cathodes of diodes 191-1 and 191-2 having the same IV conversion characteristics (current voltage conversion characteristics) as the diodes 171 and 172 are connected to a power source higher than the reference potential via the terminal 118. Then, an anode of the diode 191-1 is connected to the electrode 111-1, the gate of the amplifying transistor configuring the amplifier 112, and the cathode of the diode 172. Furthermore, an anode of the diode 191-2 is connected to the electrode 111-11, the reference potential generating unit 119, and the cathode of the diode 171.

Figure 6:
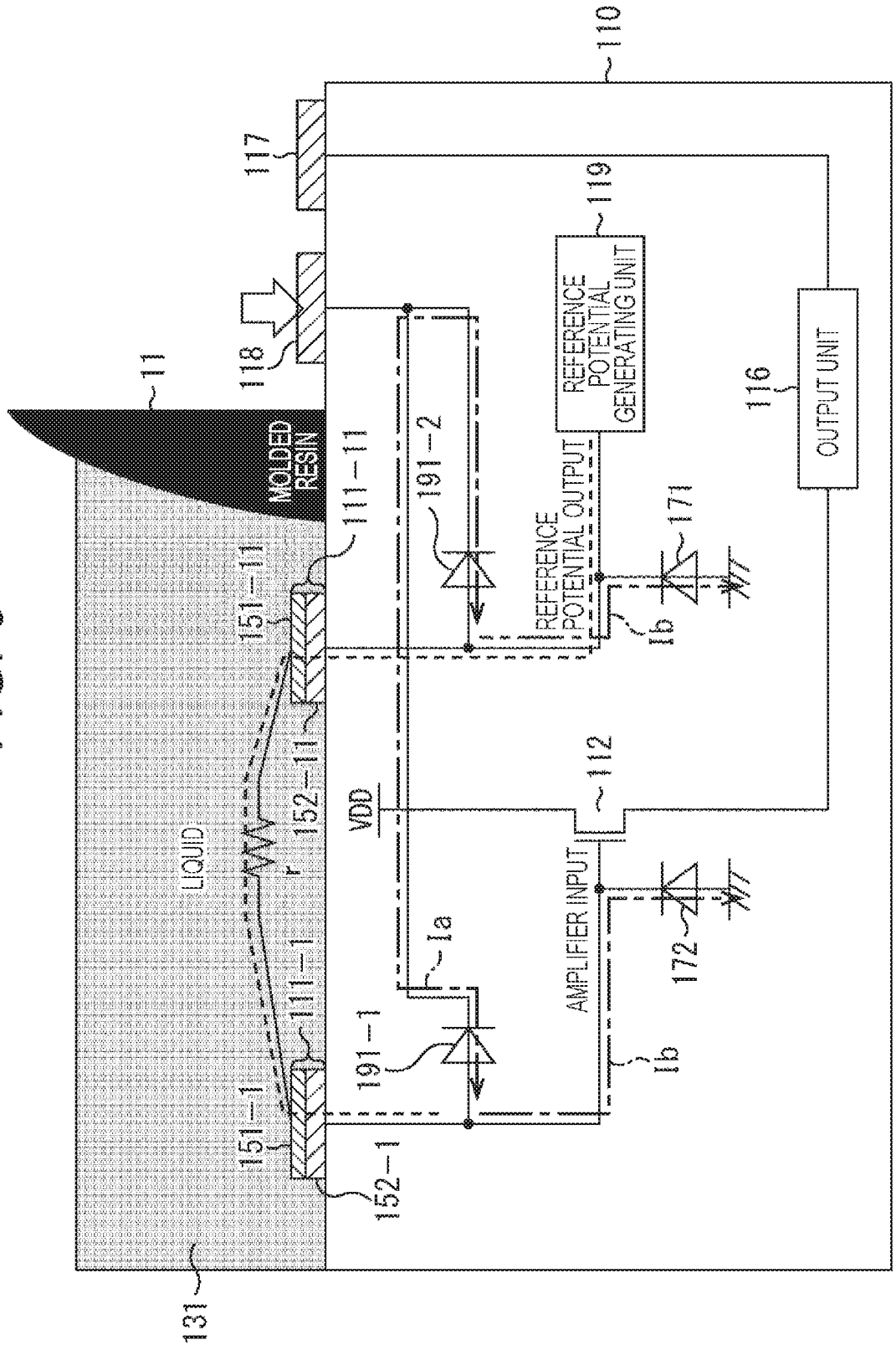
FIG. 6 is a diagram for explaining an operation of the second protection circuit of the potential measuring apparatus in FIG. 2.

With such a configuration, the diodes 191-1 and 172 having the equal characteristics are connected in series, and similarly, the diodes 191-2 and 171 having the equal characteristics are connected in series. As a result, as illustrated in FIG. 6, when the leakage currents Ia and Ib indicated by the alternate long and short dash lines are equal to each other, the potentials of the electrodes 111-1 and 111-11 are substantially the same, and the leakage current indicated by the dotted line is not flowed by the internal resistance r. Therefore, the input voltage to the gate of the amplifying transistor configuring the amplifier 112 can be stabilized.

Note that, by generating the diodes 171 and 172 and the diodes 191-1 and 191-2 in the same semiconductor process, it is possible to suppress an increase in the number of processes of a manufacturing process.

<Third Protection Circuit in Potential Measuring Apparatus>

In the above, an example has been described in which the cathodes of the diodes 191-1 and 191-2 are connected to the power source higher than the reference potential via the terminal 118. However, it is possible not to use the external power by connecting the cathodes to the power source VDD of the amplifier 112 in the circuit having the similar voltage.

Figure 7:
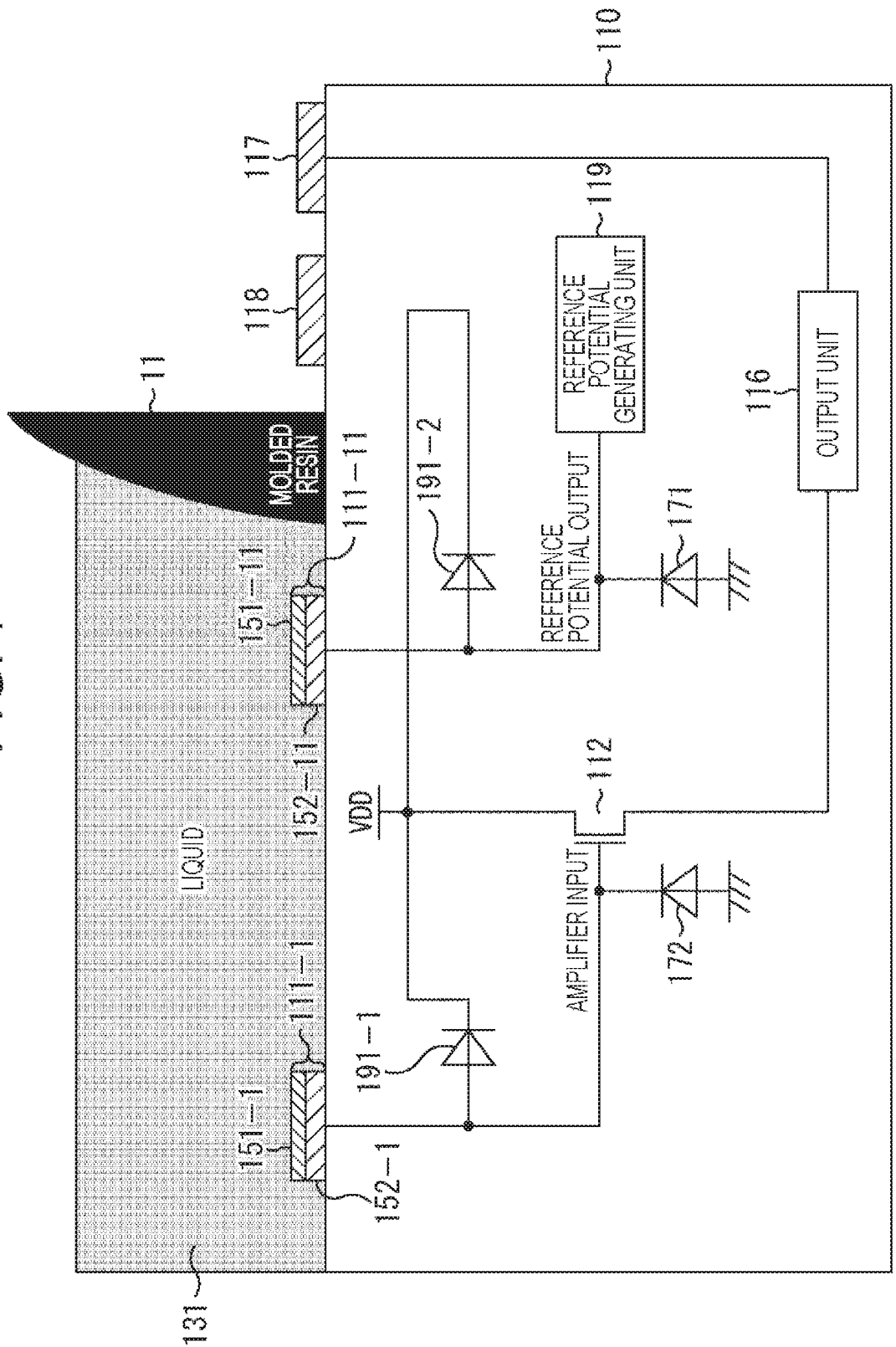
FIG. 7 is a diagram for explaining an exemplary configuration of a third protection circuit of the potential measuring apparatus in FIG. 2.

In other words, as illustrated in FIG. 7, the cathodes of the diodes 191-1 and 191-2 are connected to the power source VDD of the amplifier 112 higher than the reference potential, instead of the terminal 118.

Figure 8:
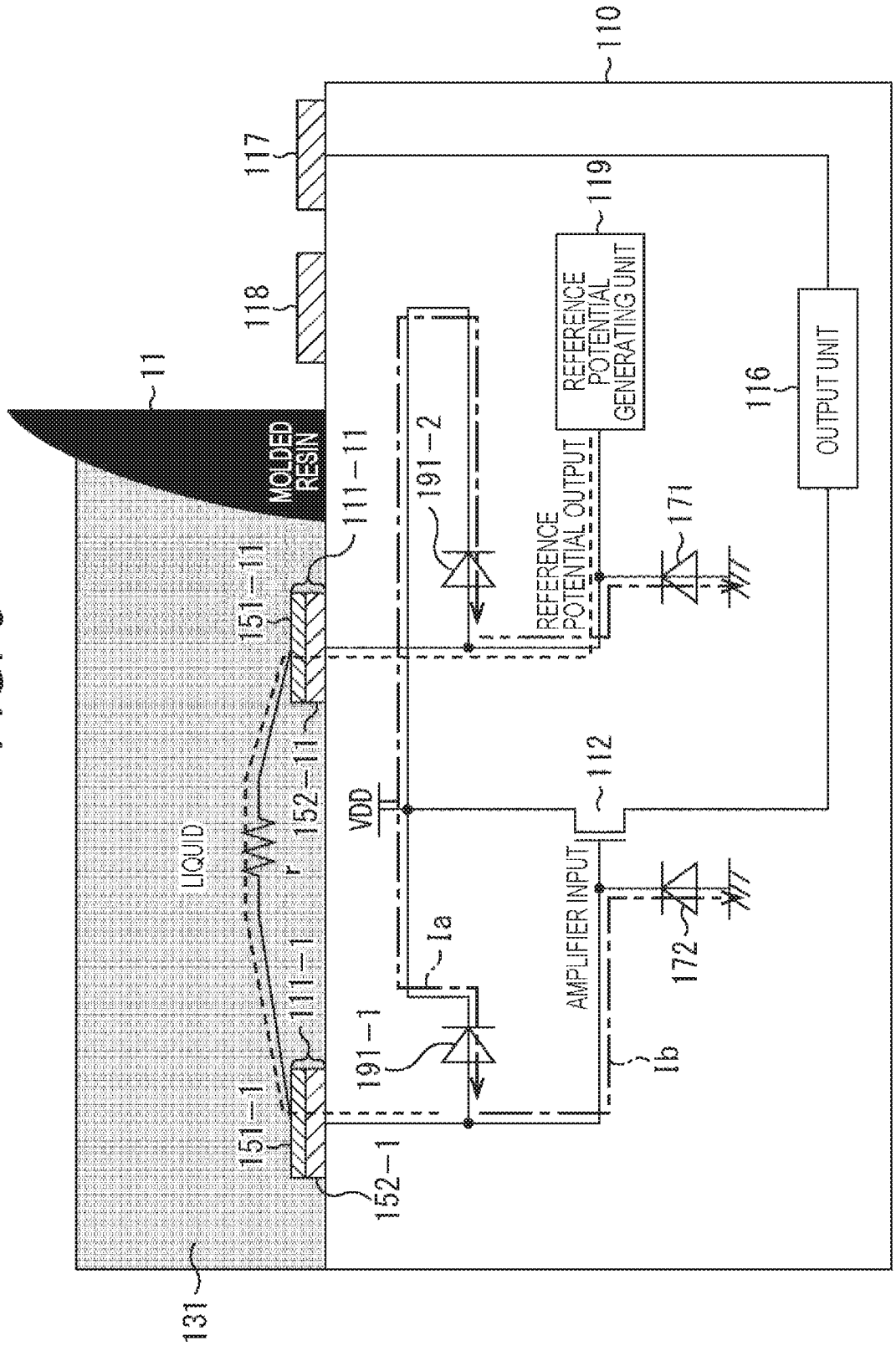
FIG. 8 is a diagram for explaining an operation of the third protection circuit of the potential measuring apparatus in FIG. 2.

Similarly, with such a configuration, the diodes 191-1 and 172 having the equal characteristics are connected in series, and the diodes 191-2 and 171 having the equal characteristics are connected in series. Therefore, as illustrated in FIG. 8, when the leakage currents Ia and Ib indicated by the alternate long and short dash lines are equal to each other, the potentials of the electrodes 111-1 and 111-2 are substantially the same, and the leakage current indicated by the dotted line is not flowed by the internal resistance r. Therefore, the input voltage to the gate of the amplifying transistor configuring the amplifier 112 can be stabilized.

<Modification>

In the above, as illustrated in FIG. 2, an example has been described in which the electrodes 111-1 to 111-4 and 111-11, the amplifiers 112-1 to 112-4, and the reference potential generating unit 119 are formed on the same substrate. However, if the electrode 111, the amplifier 112, and the reference potential 119 are formed in the same substrate, a configuration other than the configuration in which the electrodes 111-1 to 111-4 are arranged in two rows and two columns as illustrated in FIG. 2 may be used. For example, an electrode configuration in which electrodes are arranged in n rows and m columns may be used. Furthermore, the number of electrodes 111-11 used to supply the reference potential may be equal to or more than one.

Figure 9:
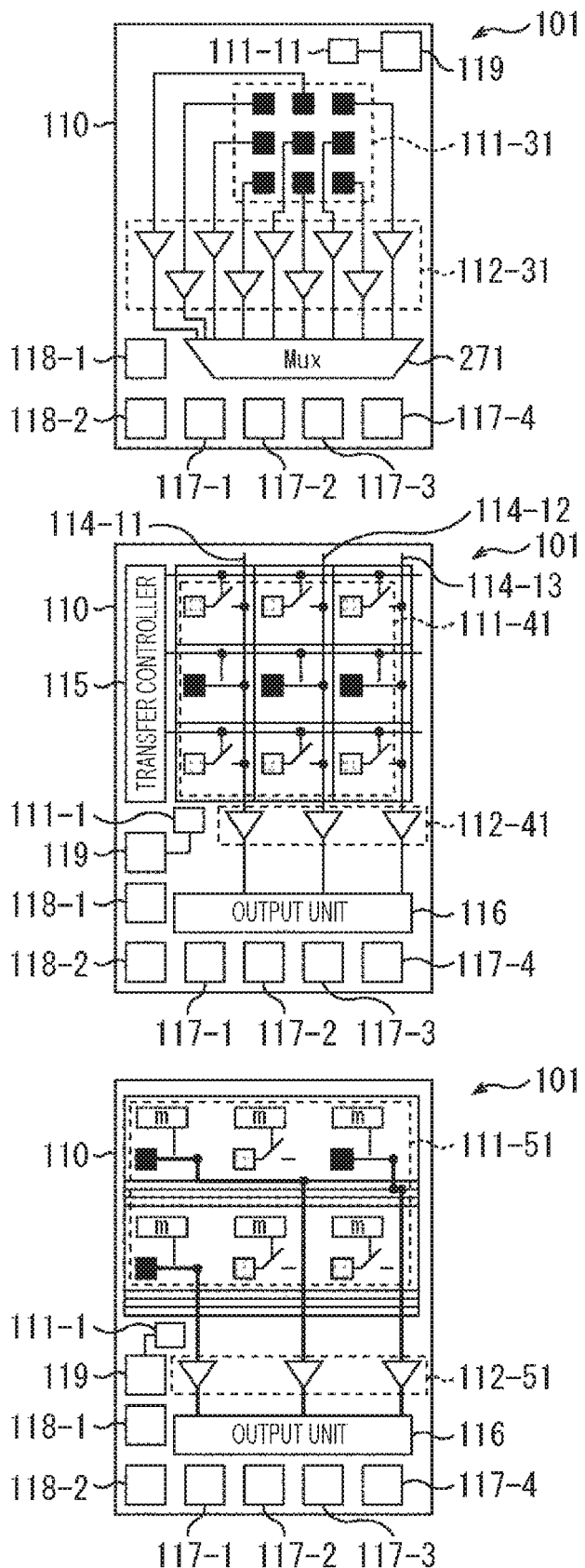
FIG. 9 is a diagram for explaining a modification of the potential measuring apparatus according to the present disclosure.

Furthermore, as illustrated in an upper part of FIG. 9, a configuration may be used in which an electrode group 111-31 including black electrodes arranged in an array of three rows and three columns and an amplifier group 112-31 of which amplifiers are respectively connected to the electrodes are included, the electrode group 111-31 and the amplifier group 112-31 are connected to a multiplexer (Mux) 271, and the multiplexer 271 time-divisionally outputs output signals.

Moreover, as illustrated in a middle part of FIG. 9, a configuration may be used in which an electrode group 111-41 including electrodes arranged in an array of three rows and three columns is controlled by the transfer controller 115 in unit of three rows, outputs are transferred to the three vertical transfer lines 114-11 to 114-13, are amplified by an amplifier group 112-41 including amplifiers respectively provided on the vertical transfer lines 114-11 to 114-13, and are output to the output unit 116. However, in the middle part of FIG. 9, three gray electrodes arranged in the upper and the lower stages in FIG. 9 are controlled to be turned on or off by switches. However, three black electrodes in the middle stage do not have a switch and constantly perform output.

Furthermore, as illustrated in the lower part of FIG. 9, a configuration may be used in which a lower left black electrode, an upper left electrode, and an upper right electrode, that is, three electrodes in total of the electrode group 111-51 including electrodes arranged in an array of three rows and two columns are respectively connected to three amplifiers of the amplifier group 112-51. Note that, in the lower part of FIG. 9, each electrode included in the electrode group 111-51 includes a local memory denoted with "m" in FIG. 9.

Note that, the present disclosure may have the following configuration.

<1> A semiconductor apparatus including:
a reference potential generating unit and a reference potential electrode configured to supply a reference potential to liquid;
a read electrode and an amplifier configured to read a signal from the liquid; and
a protection portion configured to protect the amplifier from a negative charge at a previous stage of the amplifier, in which
the reference potential generating unit, the reference potential electrode, the read electrode, the amplifier, and the protection portion are installed on a same substrate.

<2> The semiconductor apparatus according to <1>, in which
the protection portion bypasses the generated negative charges to the amplifier via a wiring connected to the read electrode and the reference potential electrode at a time of an electrode formation process for forming the read electrode and the reference potential electrode to protect the amplifier.

<3> The semiconductor apparatus according to <2>, in which
the amplifier is an amplifying transistor,
the read electrode is connected to a gate of the amplifying transistor, and
the protection portion is a protection diode of which a cathode is connected to a previous stage of the gate on the wiring for connecting the read electrode and the amplifying transistor, and an anode is grounded.

<4> The semiconductor apparatus according to <3>, further including:
an additional protection portion, of which an anode is connected to the cathode of the protection diode, a cathode is connected to a predetermined power source, having IV (current voltage) characteristics same as the protection diode.

<5> The semiconductor apparatus according to <4>, in which
a voltage of the predetermined power source is higher than the reference potential.

<6> The semiconductor apparatus according to <5>, in which the predetermined power source is a power source of the amplifying transistor.

<7> The semiconductor apparatus according to any one of <3> to <6>, further including:
another protection portion configured to protect the amplifier from a negative charge at a previous stage of the reference potential generating unit.

<8> The semiconductor apparatus according to <7>, in which
the another protection portion bypasses the generated negative charge to the reference potential generating unit via wiring connected to the reference potential electrode and the reference potential generating unit at a time of an electrode formation process for forming the read electrode and the reference potential electrode to protect the reference potential generating unit.

<9> The semiconductor apparatus according to <8>, in which
the another protection portion is another protection diode of which a cathode is connected to a previous stage of the reference potential generating unit on the wiring for connecting the reference potential electrode and the reference potential generating unit and an anode is grounded.

<10> The semiconductor apparatus according to <9>, further including:
another additional protection portion, of which an anode is connected to the cathode of the diode, a cathode is connected to a predetermined power source, having IV (current voltage) characteristics same as the another protection diode.

<11> The semiconductor apparatus according to <10>, in which
a voltage of the predetermined power source is higher than the reference potential.

<12> The semiconductor apparatus according to <11>, in which
the predetermined power source is a power source of the amplifying transistor.

<13> A potential measuring apparatus including:
a reference potential generating unit and a reference potential electrode configured to supply a reference potential to liquid;
a read electrode and an amplifier configured to read a signal from the liquid; and
a protection portion configured to protect the amplifier from a negative charge at a previous stage of the amplifier, in which
the reference potential generating unit, the reference potential electrode, the read electrode, the amplifier, and the protection portion are installed on a same substrate.

REFERENCE SIGNS LIST

101 Potential measuring apparatus
111, 111-1 to 111-5, 111-11 Electrode
112, 112-1 to 112-4 Amplifier
113-1 to 113-4 Switch
114, 114-1 to 114-3 Vertical transfer line
115 Transfer controller
116 Output unit
117, 117-1 to 117-4 Terminal
118 Terminal
119 Reference potential generating unit
131 Liquid
151, 151-1, 151-11 Plating portion
152, 152-1, 152-11 Metal portion
171, 171-1, 171-2 Diode
191, 191-1, 191-2 Diode
231, 231-1, 231-2 Diode
251, 251-1, 251-2 Diode

The invention claimed is:

1. A semiconductor apparatus comprising:
a reference potential generating unit and a reference potential electrode configured to supply a reference potential to liquid;
a read electrode and an amplifier configured to read a signal from the liquid; and
a protection portion configured to protect the amplifier from a negative charge at a previous stage of the amplifier, wherein
the reference potential generating unit, the reference potential electrode, the read electrode, the amplifier, and the protection portion are installed on a same substrate.

2. The semiconductor apparatus according to claim 1, wherein
the protection portion bypasses the generated negative charges to the amplifier via a wiring connected to the read electrode and the reference potential electrode at a time of an electrode formation process for forming the read electrode and the reference potential electrode to protect the amplifier.

3. The semiconductor apparatus according to claim 2, wherein
the amplifier is an amplifying transistor,
the read electrode is connected to a gate of the amplifying transistor, and
the protection portion is a protection diode of which a cathode is connected to a previous stage of the gate on the wiring for connecting the read electrode and the amplifying transistor, and an anode is grounded.

4. The semiconductor apparatus according to claim 3, further comprising:
an additional protection portion, of which an anode is connected to the cathode of the protection diode, a cathode is connected to a predetermined power source, having IV (current voltage) characteristics same as the protection diode.

5. The semiconductor apparatus according to claim 4, wherein
a voltage of the predetermined power source is higher than the reference potential.

6. The semiconductor apparatus according to claim 5, wherein
the predetermined power source is a power source of the amplifying transistor.

7. The semiconductor apparatus according to claim 3, further comprising:
another protection portion configured to protect the amplifier from a negative charge at a previous stage of the reference potential generating unit.

8. The semiconductor apparatus according to claim 7, wherein
the another protection portion bypasses the generated negative charge to the reference potential generating unit via wiring connected to the reference potential electrode and the reference potential generating unit at a time of an electrode formation process for forming the read electrode and the reference potential electrode to protect the reference potential generating unit.

9. The semiconductor apparatus according to claim 8, wherein
the another protection portion is another protection diode of which a cathode is connected to a previous stage of the reference potential generating unit on the wiring for connecting the reference potential electrode and the reference potential generating unit and an anode is grounded.

10. The semiconductor apparatus according to claim 9, further comprising:
another additional protection portion including another additional diode, of which an anode is connected to the cathode of the diode, a cathode is connected to a predetermined power source, having IV (current voltage) characteristics same as the another protection diode.

11. The semiconductor apparatus according to claim 10, wherein
a voltage of the predetermined power source is higher than the reference potential.

12. The semiconductor apparatus according to claim 11, wherein
the predetermined power source is a power source of the amplifying transistor.

13. A potential measuring apparatus comprising:
a reference potential generating unit and a reference potential electrode configured to supply a reference potential to liquid;
a read electrode and an amplifier configured to read a signal from the liquid; and
a protection portion configured to protect the amplifier from a negative charge at a previous stage of the amplifier, wherein
the reference potential generating unit, the reference potential electrode, the read electrode, the amplifier, and the protection portion are installed on a same substrate.

* * * * *